(12) United States Patent
Brasch et al.

(10) Patent No.: US 7,777,046 B2
(45) Date of Patent: Aug. 17, 2010

(54) METHOD OF SYNTHESIS OF A SALT OF N-ACETYL-L-CYSTEINYLCOBALAMIN

(75) Inventors: Nicola E Brasch, Kent, OH (US); Edward Suarez-Moreira, Kent, OH (US)

(73) Assignee: Kent State University, Kent, OH (US)

( * ) Notice: Subject to any disclaimer, the term of this patent is extended or adjusted under 35 U.S.C. 154(b) by 118 days.

(21) Appl. No.: 11/725,861

(22) Filed: Mar. 20, 2007

(65) Prior Publication Data

US 2008/0234489 A1      Sep. 25, 2008

(51) Int. Cl.
*C07F 15/06* (2006.01)
(52) U.S. Cl. ..................................... 548/108
(58) Field of Classification Search .................. 548/103; 424/9.362, 9.61; 540/145; 534/15
See application file for complete search history.

(56) References Cited

U.S. PATENT DOCUMENTS 7,030,105 B2 *   4/2006   Brasch et al. ............... 514/185

OTHER PUBLICATIONS

Brasch et al.,Journal of Inorganic Biochemistry, 1999, vol. 76, pp. 197-209.*

* cited by examiner

*Primary Examiner*—Yong Chu
(74) *Attorney, Agent, or Firm*—Hudak, Shunk & Farine Co. LPA

(57) ABSTRACT

The invention provides a method for preparing the sodium salt of the novel thiol derivative of vitamin $B_{12}$, N-acetyl-L-cysteinylcobalamin (Na[NACCbl]). The method involves carrying out the reaction in aqueous solvent with a relatively small excess of ligand reactant, specifically from one to less than four molar equivalents. The cobalamin derivative formed is precipitated from the aqueous solvent, preferably by the addition of a precipitate inducing solvent. This provides a product in acceptable purity without the need for an additional chromatographic purification step.

20 Claims, 1 Drawing Sheet

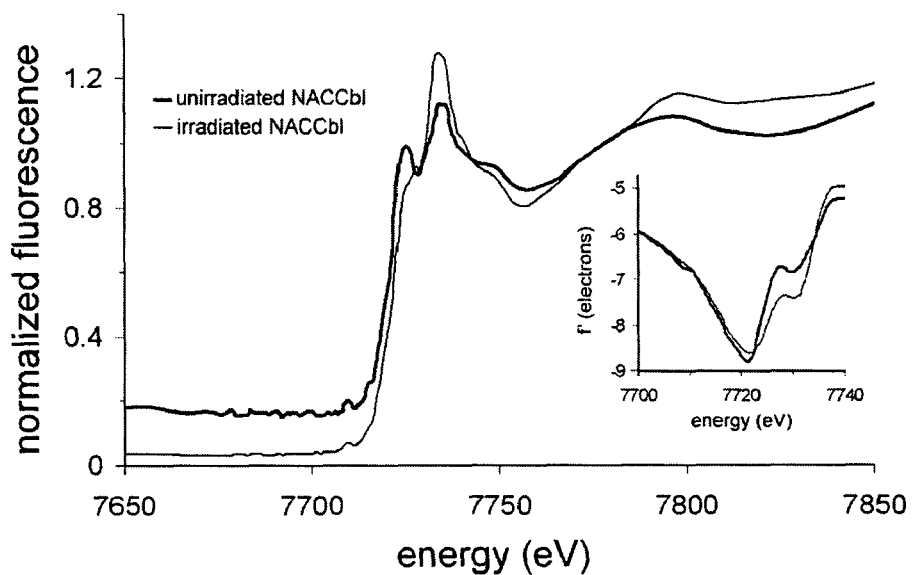
FIGURE 1
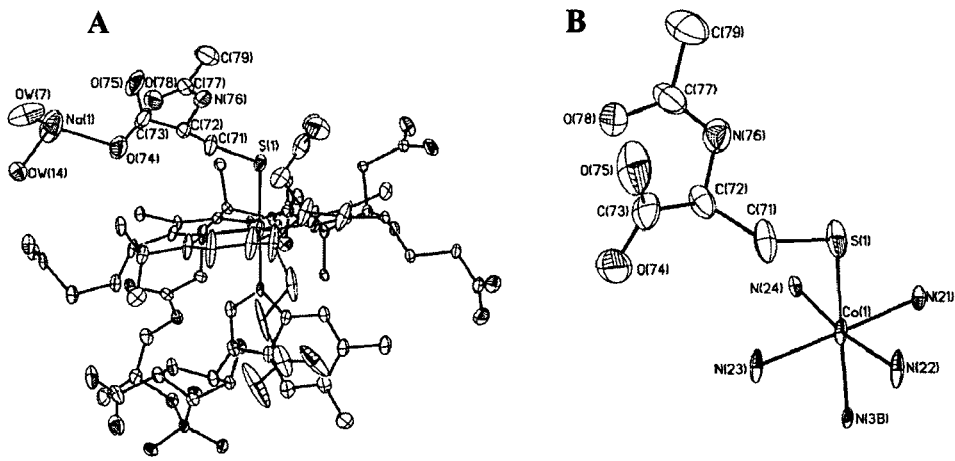
FIGURE 2  FIGURE 3

METHOD OF SYNTHESIS OF A SALT OF N-ACETYL-L-CYSTEINYLCOBALAMIN

FIELD OF THE INVENTION

The present invention relates to the synthesis of the sodium salt of the novel vitamin $B_{12}$ derivative N-acetyl-L-cysteinyl-cobalamin (Na[NACCbl]).

BACKGROUND

Corrinoid-dependent enzymes are widespread in nature and play key roles in human, animal and microbial metabolism. Two known vitamin $B_{12}$-dependent enzymes exist in humans: methylcobalamin (MeCbl)-dependent methionine synthase and adenosylcobalamin (AdoCbl)-dependent methylmalonyl-coenzyme A mutase. The clinical hallmarks of a vitamin $B_{12}$ deficiency are megaloblastic anemia ('pernicious anemia') and/or neuropathies. The $B_{12}$-dependent enzyme reactions play a vital role in maintaining healthy nerve and red blood cells and are required for the synthesis of DNA. Formula I gives the structure of the two coenzyme forms of vitamin $B_{12}$ and related $B_{12}$ derivatives (cobalamins) which have been isolated from human cells, blood or tissue. The α (or lower) axial site is occupied by an intramolecularly-bound 5,6-dimethylbenzimidazole, and the β (or upper) axial site can be occupied by a variety of ligands.

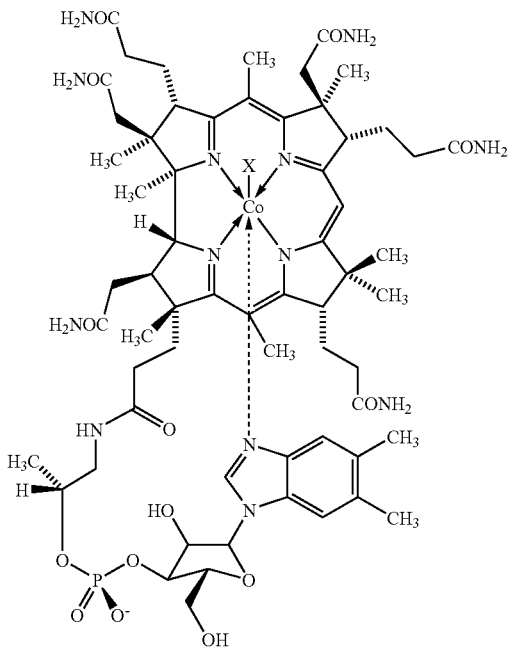

Formula I: Structures of cobalamin metabolites isolated from humans
(I) X = CN⁻ cyanocobalamin (vitamin $B_{12}$)
(II) X = $H_2O$/OH⁻ aquacobalamin/hydroxycobalamin
(III) X = $CH_3$ methylcobalamin
(IV) X = 5'-deoxyadenosyl adenosylcobalamin (coenzyme $B_{12}$)
(V) X = glutathione glutathionylcobalamin
(VI) X = $SO_3^{2-}$ sulfitocobalamin
(VII) X = $NO_2^-$ nitrocobalamin Upon reaching cells, cobalamin derivatives are converted to MeCbl (III) and AdoCbl (IV) by currently ill-defined mechanisms. Many studies have been carried out over the past several decades involving the extraction and identification of cobalamins from mammalian cells, tissue and blood, in addition to other biological samples such as foods and seaweed. AdoCbl, MeCbl and aquacobalamin (II, $H_2OCbl^+ \rightleftharpoons HOCbl + H^+$; $pK_a$=7.8) are the major cobalamin metabolites isolated from biological samples (Jacobsen, D. W., et al, *Method. Enzymol.*, 1986, 123, 14-22). Sulfitocobalamin ($SO_3Cbl^-$, VI) is also isolable from mammalian cells and foods (see Jacobsen et al, above), and there are also reports of the isolation of nitrocobalamin ($NO_2Cbl$, VII) from biological sources (Anes, J. M., et al, *J. Chromatogr. B Biomed. Appl.*, 1994, 660, 180-85). Whether or not cyanocobalamin (I) is truly "naturally occurring" is controversial; some studies report small amounts of this derivative, especially in smokers (Koyama, K., et al, *Nephrol. Dial. Transplant.*, 1997, 12, 1622-28).

Thiol derivatives of $B_{12}$, thiolatocobalamins (X=thiol, Formula I) were first identified in the 1960s, but have not attracted much attention until recently. Glutathionylcobalamin (GSCbl, V) is a naturally occurring intracellular form of cobalamin. Formation of GSCbl from $H_2OCbl^+$ and glutathione is irreversible ($K_{obs} \sim 3 \times 10^8$ $M^{-1}$ at pH 7.4, 25° C.) and rapid (t½~3 s for [GSH]=5 mM, pH 7.4, 37° C.) (Xia, L., et al, *Inorg Chem.*, 2004, 43, 6848-57). This compound is an important cobalamin metabolite in mammals; it is more readily absorbed and retained longer than cyanocobalamin, and is more active than other cobalamins in promoting methionine synthase activity in rabbit spleen extracts (Pezacka, E., et al, *Biochem. Biophys. Res. Comm.*, 1990, 169, 443-50). It has been proposed that, in vivo, GSCbl is an intermediate in the conversion of biologically inactive cobalamin forms to the active coenzyme forms adenosylcobalamin (IV) and methylcobalamin (III) (see Pezacka et al, above). The reducing agent glutathione (GSH) is required for the formation of GSCbl, and is present in lower levels under oxidative stress conditions. An alternative role for GSCbl was also recently proposed, in which the formation of GSCbl prevents $B_{12}$ from being scavenged by xenobiotics (Watson, W. P., et al, *Chem. Res. Toxicol.*, 2004, 17, 1562-67). In addition, McCaddon and co-workers suggested that GSCbl and related thiolatocobalamins might be more effective than currently available pharmaceutical $B_{12}$ forms (CNCbl and $H_2OCbl^+$) in treating of $B_{12}$-related conditions associated with oxidative stress such as Alzheimer's disease (McCaddon, A., et al, *Neurology*, 2002, 58, 1395-99). Thus, GSCbl and other thiolatocobalamins have the potential to offer a valuable source of cobalamin in therapeutic applications requiring administration of a vitamin $B_{12}$ derivative.

The structure of the thiol N-acetyl-L-cysteine (NAC) is shown in Formula II. NAC has been used in the clinic for over 50 years as a mucolytic agent. NAC also promotes the synthesis of GSH, is an antioxidant, and may be a useful therapeutic for treatment of oxidative stress-linked

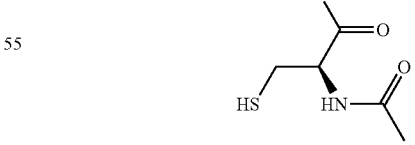

Formula II: Structure of N-acetyl-L-cysteine, diseases (Aitio, M. *Br. J. Clin. Pharm.*, 2005, 61, 5-15).

The present invention relates to the synthesis of the novel vitamin $B_{12}$ derivative N-acetyl-L-cysteinylcobalamin, Na[NACCbl]. Na[NACCbl] is characterized by a variety of techniques, including ¹H NMR and UV-vis spectroscopies and mass spectrometry. The structure of Na[NACCbl] is further verified by X-ray crystallography, and an XAS spectrum has been recorded. Na[NACCbl]) is of interest, given that it has been shown that co-administrating H₂OCbl⁺ and N-acetyl-L-cysteine improves cognitive performance in Alzheimer's patients, and the possibility that NACCbl⁻, rather than the individual compounds themselves, is responsible for the beneficial effects of this approach.

The prior art describes a method of preparing GSCbl by reacting a 1:1 ratio hydroxocobalamin (=hydroxycobalamin or aquacobalamin) and glutathione in water and precipitating the resulting complex to give a product of at least 95% purity (GB 945722 (1964 to Merck & Co., Inc.)). However, the technical sophistication available today for determining product purity was not available at the time of this earlier work and subsequent repeated attempts of this work have identified that the resulting product is in fact of only 60-70% purity. More recently, other methods for preparing GSCbl in high purity have been reported (Pezacka, E., et al, *Biochem. Biophys. Res. Commun.*, 1990, 169, 443-50; Brown K., et al, *Biochem.*, 1993, 32, 8421-28; Brasch N., et al, *Inorg. Chem.*, 1999, 76, 197-209) using a large excess of glutathione (5-12×); however, an additional chromatographic step is required to provide a product of 98% purity. One of the present inventors previously developed procedures for synthesizing and isolating the thiolatocobalamins γ-glutamyl-cysteinylcobalamin and glutathionylcobalamin in aqueous solution in high yield and purity by the addition of a small excess of thiol to a highly concentrated solution of aquacobalamin, followed by the addition of acetone to precipitate the product after completion of the reaction (Suto, R. K., et al, *Inorg. Chem.*, 2001, 40, 2686-92; U.S. Pat. No. 7,030,105). This patent presented a method of preparing GSCbl of an acceptable purity level which does not require the cost and effort of a chromatographic purification step. It is performed in the presence of air. A similar procedure was also used to synthesize pentafluorophenylthiolatocobalamin and cyclohexylthiolatocobalamin in methanol under anaerobic conditions (Brasch, N. E., et al, *J. Inorg. Biochem.*, 1999, 76, 197-209; Hsu, T.-L. C., et al, *Inorg. Chem.*, 1998, 37, 5109-5116).

SUMMARY OF THE INVENTION

In accordance with the present invention the novel and biologically relevant thiolatocobalamin derivative, Na[NACCbl], is synthesized and isolated in high purity (>95%) and in good yield (>70%). The synthesis is carried out in aqueous solution by the addition of a small excess of thiol to a highly concentrated solution of aquacobalamin, followed by the addition of acetone to precipitate the product after completion of the reaction.

Accordingly, the invention provides a method for preparing the sodium salt of N-acetyl-L-cysteinylcobalamin (Na [NACCbl]) comprising the steps of:

a) reacting a salt of hydroxycobalamin with from 1.1 to about 3.0 equivalents of N-acetyl-L-cysteine more preferably from about 1.1 to about 2 equivalents (most preferably about 1.1 to 1.5 equivalents) in an aqueous solvent;

b) precipitating the formed Na[NACCbl] from the aqueous solvent, optionally by the addition of a precipitate inducing solvent; and c) collecting the precipitated Na[NACCbl];

wherein all of the above steps are carried out in air.

BRIEF DESCRIPTION OF THE DRAWINGS

FIG. 1 is a thermal ellipsoid plot (30%) of Na[NACCbl]•18H₂O and is a view of the entire cobalamin complex.

FIG. 2 is a close up view of the N-acetyl-L-cysteine ligand from FIG. 1; and

FIG. 3 is an X-ray absorption spectrum of unradiated and radiated Na[NACCbl]•18H₂O between 7500 and 7900 eV.

DESCRIPTION OF THE PREFERRED EMBODIMENTS

Accordingly, the invention provides a method for preparing the sodium salt of N-acetyl-L-cysteinylcobalamin (Na [NACCbl]) which involves reacting a salt of hydroxycobalamin with a slight excess (i.e. from about 1.1 to about 2 or about 1.5, and preferably from about 1.1 to about 1.5 of equivalents) of N-acetyl-L-cysteine in an aqueous solvent; precipitating the formed Na[NACCbl] from the aqueous solvent, preferably by the addition of a precipitate inducing solvent; and collecting the precipitated Na[NACCbl] and all of the above steps are carried out under aerobic conditions.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

As used herein, a salt of hydroxycobalamin refers to a compound H₂OCbl.X (or HOCbl.HX) wherein X is a counter anion such as a halide (particularly Cl⁻) or an O-acyl group such as acetate.

The reaction is performed in an aqueous solvent, being water alone or a mixture of water and a water miscible solvent (such as MeOH, EtOH, PrOH & BuOH). Preferably the aqueous solvent is water alone. Where the reaction is carried out in a mixture of water and water miscible solvent, the proportion of water to water miscible solvent may depend on the kinetics and/or thermodynamics of the reaction. The reaction mixture may also optionally contain additional agents such as buffers, for example, MES. The resultant cobalamin derivatives may be slightly light-sensitive, therefore, preferably, the reaction is carried out under red light only conditions.

The reaction may be performed at a temperature from 0° to about 60°. In a preferred form of the invention, the reaction may be carried out at ambient room temperature, such as from about 15° C. to about 30° C., for example about 20-25° C.

The reaction is allowed to proceed for a time sufficient to achieve substantial completion. Reference to substantial completion of the reaction is intended to refer to the substantial consumption (e.g. greater than 95%) of the HOCbl.HX.

Precipitation of the resultant products may be performed under cooling, for example ice cooling, eg to about −20 to 10° C. However, yield of the cobalamin products can be increased by the addition of a precipitate inducing solvent. The precipitate inducing solvent used to precipitate the formed Na[NACCbl], which is preferably a water miscible solvent less polar then water and includes alcohols (such as MeOH, EtOH, PrOH & BuOH) and acetone, is added in an amount sufficient to induce precipitation of the formed Na[NACCbl]. A preferred precipitate inducing solvent is acetone.

Preferred methods of the invention provide a final product with greater than 90% purity, preferably greater than about 95% purity, more preferably 97, 98 or 99% purity as determined by the any of methods described herein such as, for example, ¹H NMR spectroscopy or the dicyanocobalamin test described by Barker et al, *J. Biol. Chem.* 1960, 135, 181-90 incorporated herein by reference as if fully set forth herein.

In a preferred form of the invention, the precipitated Na[NACCbl] is collected by filtration, preferably under suction, and optionally washing the precipitate with a suitable solvent or mixture of solvents such as acetone and/or ether. In another embodiment of the invention, the precipitate can be collected by decanting off the solvents or removing them by suction. Preferably, the precipitate is further dried to remove any remaining solvent. This may be carried out by under vacuum, optionally with heating (at a temperature which does not decompose the Na[NACCbl], for example from about 25-50° C.).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following Examples which are intended for the purpose of illustration only and are not intended to limit the generality hereinbefore described.

EXAMPLES

Hydroxycobalamin hydrochloride (HOCbl.HCl), 98% (stated purity by manufacturer) was purchased from Fluka. The percentage of water in HOCbl.HCl (.nH$_2$O) (batch-dependent, typically 10-15%), was determined by converting HOCbl.HCl to dicyanocobalamin, (CN)$_2$Cbl$^-$(0.10 M KCN, pH 10.0, $\epsilon_{368}$=30.4M$^{-1}$ cm$^{-1}$, Barker, H. A., et al, *J. Biol. Chem.*, 1960, 235, 181-90). MES and N-acetyl-L-cysteine were obtained from Sigma. Water was purified using a Barnstead Nanopure Diamond water purification system and/or HPLC grade water. All thiol solutions were prepared directly before use.

pH measurements were made with a Corning Model 445 pH meter in conjunction with a Mettler-Toledo Inlab 423 electrode at room temperature. The electrode was filled with 3 M KCl/saturated AgCl solution, pH 7.0. The electrodes were standardized with standard BDH buffer solutions at pH 4.01 and 6.98. Solution pH was adjusted using HCl or NaOH solutions as necessary.

$^1$H NMR spectra were recorded on an Inova 500 MHz or a Bruker 400 MHz spectrometer equipped with a 5 mm probe at room temperature (22±1° C.). TSP (3-(trimethylsilyl)propionic-2,2,3,3-d$_4$ acid, sodium salt) was used as an internal standard. UV-visible spectra were recorded on a Cary 5000 spectrophotometer equipped with a thermostatted cell changer (25.0±0.1° C.), operating with WinUV Bio software (version 3.00). Electrospray mass spectra were recorded using a BRUKER Esquire-LC mass spectrometer in the positive mode.

Synthesis of N-acetyl-L-cysteinylcobalamin (Na[NACCbl])

All syntheses were carried out under aerobic conditions, notwithstanding the potential light sensitivity of thiolatocobalamins.

Example 1

A solution of N-acetyl-L-cysteine (263 μml, 284 mM, 74.7 μmol, 1.1 mol equiv.) in MES buffer (0.1 M, pH ~6) was added drop wise to a solution of HOCbl.HCl (107 mg, 68 μmol, since HOCbl.HCl typically contains ~12% H$_2$O) in MES buffer (0.80 ml, 0.1 M, pH ~6) with stirring, and the reaction was allowed to react for 30 min at 0° C. The product precipitated upon dripping into a chilled acetone solution (−20° C.), and was filtered, washed with chilled acetone (20 ml, −20° C.) and diethyl ether (10 ml, −20° C.). The product was dried at 50° C. under vacuum (2×10$^{-2}$ mbar) overnight. Yield: 90 mg (87%). The purity (by $^1$H NMR spectroscopy, see below) was ~98%. The percentage of non-corrinoid products (salts) in the product can be determined by converting the thiolatocobalamin to dicyanocobalamin after drying the product at 50° C. under vacuum ($\lambda_{367nm}$=30.4 mM$^{-1}$ cm$^{-1}$), and was found to be ≦5%.

Example 2

A solution of N-acetyl-L-cysteine (15.19 mg, 263 μL, 93.1 μmol) in water was added drop wise to a HOCbl.HCl solution (108.3 mg of HOCbl.HCl, 69 μmol, 0.800 mL) in water. This mixture was stirred, and the reaction was allowed to react for 30 min at 0° C. The product precipitated upon dripping into chilled acetone (−20° C.), and was filtered and washed with chilled acetone (20 mL, −20° C.). The product was dried at 50° C. under vacuum (2×10$^{-2}$ mbar) overnight. Yield: 103.2 mg. Purity: ~98% ($^1$H NMR spectroscopy).

Characterization of Na[NACCbl]

1. $^1$H and UV-vis Spectroscopies

The chemical shifts of cobalamins in the aromatic region of the $^1$H NMR spectrum are dependent on the β-axial ligand (X, Formula I). Na[NACCbl] has five characteristic signals at 6.09, 6.28, 6.40, 6.95 and 7.19 ppm, Table 1. As expected, these values are similar to other thiolatocobalamins GSCbl, homocysteinylcobalamin (HcyCbl) and 2-N-acetylamino-2-carbomethoxyethanethiolatocobalamin (NACMECbl) and are shifted from those of the reactant, H$_2$OCbl$^+$ (Table 1). The cobalamin purity assessed by the aromatic region of $^1$H NMR spectrum was ~98%.

The visible wavelength maxima of cobalamins are also dependent on the β-axial ligand. Table 1 gives wavelength maxima for Na[NACCbl] and related thiolatocobalamins. The wavelength maxima of Na[NACCbl] are very similar to other thiolatocobalamins and substantially different from H$_2$OCbl$^+$, Table 1.

2. Mass Spectrometry

Na[NACCbl] was also characterized by ES-MS. m/z: 1492.3 (calcd for [NACCbl+2H]$^+$, C$_{67}$H$_{98}$CoN$_{14}$O$_{17}$PS=1491.6); 1513.9 (calcd for [NACCbl+H+Na]$^+$, C$_{67}$H$_{97}$CoN$_{14}$NaO$_{17}$PS=1513.6); 746.5 (calcd for [NACCbl+3H]$^{2+}$, C$_{67}$H$_{99}$CoN$_{14}$O$_{17}$PS=746.3); 757.7 (calcd for [NACCbl+Na+2H]$^{2+}$, C$_{67}$H$_{98}$CoN$_{14}$NaO$_{17}$PS=757.3). NaOH is added to prepare the buffer. The presence of Na$^+$ is confirmed by X-ray crystallography. Electron density which can be attributed to Na$^+$ is observed close to the cobalamin as is shown in FIG. 1.

3. X-Ray Diffraction Studies

Crystals suitable for X-ray diffraction studies were obtained for the sodium salt of N-acetyl-L-cysteinylcobalamin from a concentrated solution of HOCbl.HCl, with 2 molar equivalents of NAC and 1% NaCl in water. An aliquot

TABLE 1

UV-Vis and $^1$H NMR spectroscopy data for cobalamins at pH/pD
5.5 (0.10 M MES buffer). Electronic spectra were recorded at 25.0° C. and
NMR spectra were collected at room temperature.

| Cobalamin | UV-Vis Spectroscopy Data λ max (nm) | | | $^1$H NMR Spectroscopy Data Chemical shift (ppm) | | | | |
|---|---|---|---|---|---|---|---|---|
| | | | | B7 | B2 | B4 | R1 | C10 |
| $H_2OCbl^+$ | | 349 | 411 | 525 | 7.18 | 6.54 | 6.47 | 6.26 | 6.30 |
| GSCbl | 333 | 372 | 428 | 534 | 7.19 | 6.95 | 6.39 | 6.28 | 6.09 |
| NACCbl$^-$ | 333 | 372 | 428 | 534 | 7.19 | 6.95 | 6.40 | 6.28 | 6.09 |
| NACMECbl | 333 | 372 | 428 | 534 | 7.19 | 6.95 | 6.40 | 6.28 | 6.09 |
| HcyCbl | 333 | 372 | 428 | 534 | 7.20 | 6.95 | 6.38 | 6.28 | 6.10 | of a NAC solution (182 mM, 40 µL, in HPLC grade $H_2O$) was added to a solution of $HOCbl \cdot HCl$ (100 µL, 36 mM, in $H_2O$), NaCl (1.4 mg) added, and the solution mixed until everything dissolved. The solution was kept at room temperature in a closed glass vial protected from light. Small crystals were observed after 24 hr. Suitable crystals for X-ray diffraction studies were obtained after leaving the sample in a fridge at 4° C. for 5 days.

A crystal (~0.3×0.1×0.1 mm) was mounted under paraffin oil in a nylon loop and flash frozen in liquid nitrogen. Diffraction experiments were carried out on beamline BL11-1 at the Stanford Synchrotron Radiation Laboratory (SSRL). Data were collected on an ADSC Q-315 CCD detector using X-rays produced by a 26 pole wiggler insertion device, with a wavelength of 0.81798 Å (15160 eV) from a side scattering bent asymmetric cut Si (111) crystal monochromator. Two data sets were collected, both consisting of 90 1° images with a crystal to detector distance of 97 mm and covering the same range of phi angle. The first high-resolution pass had an exposure time of 15 s and the second pass had an exposure time of 1 s to record the strong low resolution reflections discarded from the first pass due to overloading of the CCD detector. The data were processed with the program XDS and scaled together with the program XSCALE. Bijvoet pairs were not merged and no absorption correction was applied. A total of 53901 reflections were measured to a nominal resolution of 0.77 Å, resulting in a final unique dataset of 17617 reflections with a merging R-factor of 0.105.

The structure was solved by Patterson methods to locate the cobalt, phosphorus and sulfur atoms, then the lighter atoms located by difference Fourier synthesis, as implemented in the program SHELXS. The structure was refined by full matrix least-squares methods using SHELXL. All non-hydrogen atoms were refined with anisotropic thermal parameters and hydrogen atoms were added in idealized positions and refined in riding positions. A correction for the anomalous scattering from cobalt at 15160 eV was applied during refinement. Additional difference electron density peaks were modelled as water molecules. One of the hydroxyl oxygen atoms of the ribose moiety appeared to have two distinct conformations and these were modelled with 50% occupancy. The final crystallographic R factor, R1, was 0.1023 for 16106 reflections, with $F_o > 4 \sigma F$. Additional data collection and refinement statistics are given in Table 2.

$Na[NACCbl] \cdot 18H_2O$ crystallizes in the orthorhombic space group $P2_12_12_1$ with one molecule per asymmetric unit. Analysis of the crystal packing by

TABLE 2

Crystal data and structure refinement parameters for
$Na[NACCbl] \cdot 18H_2O$

| Parameter | Value |
|---|---|
| Empirical formula | $NaC_{67}H_{132}N_{14}O_{35}PCoS$ |
| FW | 1838 g/mol |
| Temperature | 100 K |
| Wavelength | 0.817975 Å |
| Space group | $P2_12_12_1$ |
| Unit cell dimensions | a = 16.153 |
| | b = 21.076 |
| | c = 25.449 |
| Volume | 8663.8(8) Å$^3$ |
| Z | 4 |
| Absorption coefficient | 0.31 mm$^{-1}$ |
| F(000) | 3208 |
| Limiting indices | $-19 \leq h \leq 19, -25 \leq k \leq 25, -32 \leq l \leq 32$ |
| Reflections collected/unique | 53901/17617 |
| $R_{merge}$ and $R_{sym}$ | 0.105, 0.119 |
| Refinement method | Full-matrix least squares on F$^2$ |
| Data/restrains/parameters | 17617/0/1143 |
| GOF on F$^2$ | 0.986 |
| R factors (I > 4$\sigma_I$) | R1 = 0.1030, wR2 = 0.2645 |
| R factor (all data) | R1 = 0.1082 |
| Largest difference peak and hole | +1.3 and -1.1 e/Å$^3$ | comparison of the ratios of the c/a and b/a unit cell dimensions show that these crystals are typical of cluster I packing (c/a=1.575, b/a=1.305; Randaccio, L., et al, *Coord. Chem. Rev.*, 2006, 250, 1332-50. The crystal structure of the cobalamin molecule has been described exhaustively in the literature and the current $Na[NACCbl] \cdot 18H_2O$ structure, does not deviate markedly from the cobalamin structures known to date.

FIG. 1 is a thermal ellipsoid plot (30%) of Na[N-acetyl-L-cysteinylcobalamin]$\cdot 18H_2O$ presenting a view of the entire cobalamin complex. The N-acetyl-L-cysteine is bound to the Co through the sulfur atom (Co—S bond distance=2.250(3) Å) and the carboxylate O of the NAC ligand is bound to a Na$^+$ cation. Two waters bound to the Na$^+$ cation are also shown. Other solvent molecules are not shown for clarity. FIG. 2 is a close-up view of the N-acetyl-L-cysteine ligand.

The individual cobalamin molecules are oriented in the crystal such that the plane of the corrin ring is roughly parallel to the ab plane of the unit cell. However, the neighbouring cobalamin molecules are not perfectly parallel with each other, which gives rise to layers of zig-zagged planes when viewed perpendicular to the bc plane, separated by layers of solvent molecules. The axial base and the N-acetyl-L-cysteinyl ligand extend into these solvent layers. When viewed down the 2-fold screw along the c axis, long solvent channels are clearly evident. This solvent structure has been modelled in Na[NACCbl] as 18 water molecules. The majority of the solvent molecules are directly hydrogen bonded to either an oxygen or a nitrogen atom, although one water molecule is hydrogen bonded to other water molecules only. There is evidence for the presence of a sodium ion at a distance of 2.61 Å from one of the oxygen atoms (O74) of the carboxylate group of the cysteinyl ligand. Although it was initially modelled as a water molecule, it was found to be within 3 Å of five other oxygen atoms (O74 and four water molecules, at an average distance of 2.87 Å), hence it was changed to a sodium ion in the final stages of the refinement. This is consistent with the presence of a negative charge at the cysteinyl carboxylate, and the observation of a sodium ion near the glutamyl carboxylate in the γ-GluCysCbl structure (Suto, R. K., et al, *Inorg. Chem.*, 2001, 40, 2686-92). There are significant intermolecular contacts in the crystal lattice, and although there are five direct nitrogen-oxygen hydrogen bonds linking neighbouring cobalamin molecules, the majority of the interactions involve water-mediated hydrogen bonds. Although the final R-factor of 10.24% is typical of the cobalamin structures (see Suto et al, above), this could possibly be explained by a combination of inherent disorder in the crystal lattice due to the relative lack of direct contacts versus water-mediated interactions, and the presence of disorder in the solvent structure itself. Attempts were made during the latter stages of the refinement to model the disorder solvent but this gave negligible improvement to the overall R-factors.

The N-acetyl-L-cysteinyl ligand is bound to the cobalamin through the sulfur atom as expected (FIG. 3), with a Co—S bond distance of 2.250(3) Å, similar to the bond lengths observed in other Co—S containing cobalamin structures determined previously (Table 3). Furthermore, the four in-plane Co—N bonds and the axial base Co—N bond are all very similar to those reported elsewhere. Comparison of the Na[NACCbl]•18H$_2$O structure with that of γ-GluCysCbl is rather interesting, in that whereas the upward corrin fold in the latter was found to be the largest yet observed in a cobalamin structure (24.2°), the corrin fold angle in Na[NACCbl]•18H$_2$O of 17.5° is significantly less, although still slightly larger than some of the other Co—S containing cobalamins. This is rather intriguing given that the Co—S and Co—N bond lengths show very little variation between these two structures, although it was observed in the γ-GluCysCbl that there was a hydrogen bonding interaction between N40 and the cysteinyl sulfur (N—S distance of 3.41 Å), and it was suggested that this could contribute to the larger upward fold of the corrin ring (see Suto et al, above). A similar interaction could exist in Na[NACCbl]·18H$_2$O, although the orientation of the N40 and S1 atoms are not entirely optimal for hydrogen bonding, in that the C71-S1-N40 angle is close to 90° and the N—S distance is 3.55 Å. However, there could still be a weak interaction and it is conceivable that the strength of this intramolecular hydrogen bond may have an impact on the amount of pucker in the corrin ring.

4. Measurement of the Co(III) Absorption Spectrum

The cobalt absorption edge for the Na[NACCbl] sample were measured on SSRL beamline BL9-2 from the frozen crystal used for data collection (irradiated sample) and from a freshly mounted frozen crystal which had not been exposed (unirradiated sample), using X-rays produced by a 16 pole wiggler insertion device through a flat Rh coated collimating mirror, a liquid nitrogen cooled double Si(111) crystal monochromator and a toroidal focussing mirror. The spectra were collected in fluorescence mode between 7500 and 7900 eV using a Canberra/Eurisys Si drift detector with a total acquisition time of 440 s. The spectra were normalized by dividing the sample fluorescence at each point by the fluorescence at the inflection point of the first EXAFS peak (at 7.784 eV). The first derivative of the spectra were calculated using the program AUTOCHOOCH (G. Evans, et al, *J Appl. Crystallogr.*, 2001, 34, 82-86) which is based on the Kramers-Kronig transformation algorithm and the inflection point or threshold energy taken as the minimum of this transformation.

The cobalt X-ray absorption spectroscopy (XAS) spectrum from 7650 to 7850 eV for the Na[NACCbl] crystal used in the X-ray diffraction experiments (irradiated NACCbl) and a second Na[NACCbl] crystal from the same crystal batch which had not previously been exposed to X-rays (unirradiated NACCbl) are given in FIG. 3. The overall shape of the XANES region of the unirradiated Na[NACCbl] crystal is reminiscent of the XANES spectra for unirradiated CNCbl and H$_2$OCbl$^+$ (Champloy, F., et al, *J. Synchrotron Radiat.*, 2000, 7, 267-73). The XANES spectrum of the crystal used for the X-ray diffraction data collection shows a significant drop in the intensity of the first maximum, as was also previously observed for CNCbl and H$_2$OCbl$^+$ upon prolonged exposure to X-rays (see Champloy et al, above). In this study, the samples were exposed to X-rays during the collection of the XAS spectra and for extended periods in between as a simulation of typical X-ray exposure during X-ray structure

TABLE 3

Comparison of the Co coordination sphere in a number of Co—S containing cobalamins

|  | Na[NACCbl] | Na[γ-GluCysCbl][a] | [(NH$_2$)$_2$CSCbl]Cl[b] | [NCS]Cbl[c] | NH$_4$[SO$_3$Cbl][b] |
|---|---|---|---|---|---|
| Co—S | 2.25 | 2.27 | 2.22 | 2.25 | 2.23 |
| Co—N3B | 2.06 | 2.05 | 2.01 | 1.99 | 2.13 |
| Co—N21 | 1.88 | 1.89 | 1.85 | 1.89 | 1.87 |
| Co—N22 | 1.92 | 1.90 | 1.90 | 1.92 | 1.91 |
| Co—N23 | 1.93 | 1.91 | 1.91 | 1.92 | 1.89 |
| Co—N24 | 1.88 | 1.89 | 1.88 | 1.90 | 1.89 |
| corrin fold (°) | 17.5 | 24.2 | 14.9 | 14.9 | 16.3 |

[a]From R. K. Suto, N. E Brasch, O. P. Anderson and R. G. Finke, Inorg. Chem, 2001, 40 2686-2692.
[b]From reference L. Randaccio, S. Geremia, G. Nardin, M. Slouf and I. Srnova, Inorg Chem, 1999, 38, 4087-4092. Also see reference L. Randaccio, S. Geremia, M. Stener, D. Toffoli and E. Zandgrando, Eur J Inorg Chem, 2002, 1, 93-103.
[c]From reference G. Garau, S. Geremia, L. G. Marzilli, G. Nardin, L. Randaccio and G. Tauzher, Acta Crystallogr B, 2003, 59, 51-59.

data collection. In the case of Na[NACCbl], the irradiated sample was produced during normal synchrotron X-ray diffraction data collection (the total exposure time was between 25-30 min, including initial test images), and the XANES spectrum of the irradiated sample was measured subsequently to determine whether any damage had occurred. To our knowledge, the current results with Na[NACCbl] is the first reported example showing that irradiation damage does indeed occur to cobalamins during X-ray diffraction data collection. The XANES spectrum of GSCbl has also been previously reported (Scheuring, E. M., et al, *Biochemistry*, 1994, 33, 6310-15) and resembles the irradiated Na[NACCbl] XANES spectrum. In this study, XAS and EXAFS spectra were recorded 6-9 times, hence it is possible that photoreduction of the sample did occur. It has been proposed that irradiation of cobalamins may lead to mixed Co(III)/Co(II) oxidation states (see Champloy et al, above), which may ultimately be responsible for the abnormally long Co—N bond lengths observed for Cbl-bound methylmalonyl-CoA mutase and glutumate mutase as a consequence of the formation of six-coordinate Cbl(II) species (see Champloy et al, above). It is well established in protein crystallography that X-ray exposure during diffraction data collection generates free radicals which cause extensive radiation damage to the protein molecule, including cleavage of disulfide bonds, decarboxylation of acid residues, changes in crystal packing and photoreduction of metal centers in metalloproteins. (Ravelli, R. B., et al, *Structure*, 2000, 8, 315-28; Champloy, F., et al, *J. Synchrotron Radiat.*, 2000, 7, 267-73).

A change in the threshold energy has been interpreted as additional evidence for significant photoreduction by the X-ray beam (see Champloy et al, above) The threshold energy (or inflection point) of the absorption edge, calculated from the first derivative of the edge spectra (see FIG. 3) using the Kramers-Kronig algorithm implemented in AUTO-CHOOCH, is the same within experimental error (7721.3±0.2 and 7721.4±0.2, respectively) for the unirradiated and irradiated Na[NACCbl] crystals. This result combined with the reasonable Co—S and Co—N bond lengths suggest that radiation damage of Na[NACCbl] probably has a minimal effect on the Co oxidation state and the first coordination sphere ligands during X-ray data collection in this particular case. The threshold frequency has also previously been used as an indicator of the oxidation state of the cobalt center, with the threshold frequency supposedly increasing with increasing oxidation state (Chance, M. R. in *Chemistry and Biochemistry of $B_{12}$*, ed. R. Banetjee, John Wiley & Sons, New York, 1999, pp. 43-71). However, the value of 7721.3 eV obtained for unirradiated Na[NACCbl] is closer to that reported for Cbl(I) (7721.0±0.2) rather than Cbl(II) (7722.0±0.2), or the X-ray insensitive AdoCbl (7722.0±0.2) and MeCbl (7722.5±0.2), (see Champloy, F. et al, above) suggesting that the threshold frequency may not always be a good indicator of the oxidation state of the cobalt center. Values of 7721.8±0.25 and 7721.0±0.2 have been previously reported for GSCbl and cysteinylcobalamin, respectively.

FIG. 3 is an X-ray absorption spectrum of unrradiated (bold) and radiated Na[NACCbl].$18H_2O$ between 7500 and 7900 eV. The inset shows the first derivative of the spectrum, with the negative peak position (7721.3 and 7721.4 eV for the irradiated and unirradiated samples respectively) corresponding to the position of the inflection point or threshold energy.

While in accordance with the patent statutes, the best mode and preferred embodiment have been set forth, the scope of the invention is not limited thereto, but rather by the scope of the attached claims.

What is claimed is:

1. A method for preparing a salt of N-acetyl-L-cysteinylcobalamin (NACCbl$^-$) comprising:
   a) reacting a salt of hydroxycobalamin with greater than about 1 to about 3 molar equivalents of N-acetyl-L-cysteine in [an aqueous solvent] a solvent comprising water, and optionally a water miscible solvent;
   b) precipitating the formed NACCbl$^-$ optionally by the addition of a precipitate inducing solvent; and
   c) collecting the precipitated NACCbl$^-$.

2. A method according to claim 1 wherein from about 1.1 to 3.0 equivalents of N-acetyl-L-cysteine are used.

3. A method according to claim 2 wherein from about 1.1 to 2.0 equivalents of N-acetyl-L-cysteine are used.

4. A method according to claim 3 wherein from about 1.1 to 1.5 equivalents of N-acetyl-L-cysteine are used.

5. A method according to claim 1 wherein the salt of hydroxycobalamin is $H_2OCbl.Cl$ or $H_2OCbl.OAc$.

6. A method according to claim 1 wherein the aqueous solvent is water.

7. A method according to claim 1 wherein the precipitate inducing solvent is acetone.

8. A method according to claim 1 wherein the precipitate is collected by filtration.

9. A method according to claim 1 where the obtained precipitate is Na(NACCbl) which has a purity of at least 95% as determined by the 1H NMR method or the $(CN)_2$ Cbl$^-$ method.

10. A method according to claim 1 wherein the reaction is carried out at a concentration in the range of 0.001 to 0.1 M HOCbl.HX.

11. A method for preparing a product which is a salt of N-acetyl-L-cysteinylcobalamin (NACCbl$^{31}$), wherein the product is stable, the method comprising the steps of:
   a) reacting a salt of hydroxycobalamin with greater than 1 to about 3 molar equivalents of N-acetyl-L-cysteine in an aqueous solvent;
   b) precipitating the formed NACCbl$^{31}$ from the aqueous solvent, optionally by the addition of a precipitate inducing solvent; and
   c) collecting the precipitated NACCbl$^{31}$.

12. A method according to claim 11 wherein from about 1.1 to 3.0 equivalents of N-acetyl-L-cysteine are used.

13. A method according to claim 12 wherein from about 1.1 to 2.0 equivalents of N-acetyl-L-cysteine are used.

14. A method according to claim 13 wherein from about 1.1 to 1.5 equivalents of N-acetyl-L-cysteine are used.

15. A method according to claim 11 wherein the salt of hydroxycobalamin is $H_2OCbl.Cl$ or $H_2OCbl.OAc$.

16. A method according to claim 11 wherein the aqueous solvent is water.

17. A method according to claim 11 wherein the precipitate inducing solvent is acetone.

18. A method according to claim 11 wherein the precipitate is collected by filtration.

19. A method according to claim 11 where the obtained precipitate is Na(NACCbl) which has a purity of at least 95% as determined by the 1H NMR method or the $(CN)_2Cbl^-$ method.

20. A method according to claim 11 wherein the reaction is carried out at a concentration in the range of 0.001 to 0.1 M HOCbl.HX.

* * * * *

UNITED STATES PATENT AND TRADEMARK OFFICE
CERTIFICATE OF CORRECTION

Page 1 of 1

PATENT NO. : 7,777,046 B2
APPLICATION NO. : 11/725861
DATED : August 17, 2010
INVENTOR(S) : Nicola E. Brasch et al.

It is certified that error appears in the above-identified patent and that said Letters Patent is hereby corrected as shown below:

In Claim 1, column 12, line 6, delete "[an aqueous solvent]".

In Claim 5, column 12, line 18, replace "$H_2OCbl.Cl$" with --$H_2OCbl·Cl$--; same line, replace "$H_2OCbl.OAc$" with --$H_2OCbl·OAc$--.

In Claim 10, column 12, line 32, replace "$HOCbl.HX$" with --$HOCbl·HX$--.

In Claim 11, column 12, line 34, replace "$(NACCbl^{31})$" with --$(NACCbl^-)$--.

In Claim 11, column 12, line 39, replace "$NACCbl^{31}$" with --$NACCbl^-$--.

In Claim 11, column 12, line 42, replace "$NACCbl^{31}$" with --$NACCbl^=$--.

Signed and Sealed this
Twenty-second Day of March, 2011

David J. Kappos
*Director of the United States Patent and Trademark Office*